(12) United States Patent
Hafemann

(10) Patent No.: US 6,907,636 B2
(45) Date of Patent: Jun. 21, 2005

(54) DENTAL CARE DEVICE

(75) Inventor: Klaus Hafemann, Essen (DE)

(73) Assignee: Wik Far East Ltd., Hong Kong (CN)

( * ) Notice: Subject to any disclaimer, the term of this patent is extended or adjusted under 35 U.S.C. 154(b) by 267 days.

(21) Appl. No.: 10/225,888

(22) Filed: Aug. 22, 2002

(65) Prior Publication Data

US 2003/0041397 A1 Mar. 6, 2003

(30) Foreign Application Priority Data

Aug. 22, 2001 (DE) ..................... 201 13 895 U

(51) Int. Cl.$^7$ .................... A46B 13/02; A46B 15/00
(52) U.S. Cl. ....................... 15/22.4; 15/22.1
(58) Field of Search ................ 15/22.1, 22.2, 15/28, 22.4

(56) References Cited

U.S. PATENT DOCUMENTS

| 4,460,341 A | | 7/1984 | Nakanishi |
| 4,682,584 A | * | 7/1987 | Pose .......................... 600/11 |
| 5,625,916 A | | 5/1997 | McDougall |

FOREIGN PATENT DOCUMENTS

| DE | 3412601 | 10/1984 |
| DE | 34 12 601 C2 | 3/1996 |
| DE | 195 21 302 C1 | 11/1996 |
| DE | 199 37 281 A1 | 2/2001 |
| DE | 199 54 294 A1 | 5/2001 |
| DE | 201 09 552 | 9/2001 |
| DE | 1 285 637 A3 | 3/2003 |
| WO | WO 96/31171 | 10/1996 |
| WO | WO 96/37164 | 11/1996 |

* cited by examiner

Primary Examiner—Randall Chin
(74) Attorney, Agent, or Firm—Margaret Polson; Patent Law Offices of Rick Martin, P.C.

(57) ABSTRACT

An electric dental care device with a care head 7 oscillatingly driven about a rotational axis $D_V$ powered by a rotating driving shaft 2. One end of driving shaft 2 has a driving element 17 disposed eccentrically to the rotational axis of the driving shaft 2. The driving element 17 engages a recess of a force converter to convert the rotational force of the driving element 17 into an oscillatory turning movement of the care head 7. The force converter comprises a gymballed conversion element 6 which engages and supports the driving element 17. The rotational axes $D_H$, $D_V$ of the two gymbal bearings of the conversion element 6 are disposed to form a right. The conversion element 6 is swivellably supported by a mounting 8 about a first rotational axis $D_H$. The mounting 8 is supported turnably about the second rotational axis $D_V$ and carries the care head 7.

9 Claims, 2 Drawing Sheets

DENTAL CARE DEVICE

CROSS REFERENCE APPLICATIONS

This application claims priority from German application no. 201 13 895.6 filed Aug. 22, 2001.

FIELD OF INVENTION

The invention relates to an electric dental care device with a care head driven oscillatingly about a rotational axis. Other applications of this invention could include power tools especially power sanders. The care head is set into motion by a rotationally driven driving shaft with a driving element at one end disposed eccentrically with respect to the rotational axis of the driving shaft. The driving element and the care head engages a force converter converting the rotational driving force of the driving element into an oscillatory turning movement of the care head.

BACKGROUND OF THE INVENTION

Electromotor-driven dental care devices are well known in the art. This includes tooth brushes where the brush head is driven oscillatingly about a rotational axis. The care head is located at the free end of a shank of the dental care device with its other end being a handle portion. In the handle portion an electric motor is disposed with a driving shaft in the shank.

Such a dental care device is described in DE 34 12 601 C2. The driving shaft of the dental care device carries at the care head end a driving pivot disposed eccentrically with respect to the driving shaft. The longitudinal axis of the driving pivot is inclined relative to the rotational axis of the driving shaft. For the conversion of the rotational turning movement of the driving shaft into an oscillatory movement of the care head an axial gap is introduced into a driving shaft of the care head and is disposed at right angles to the driving shaft supported in the shank. The driving pivot is disposed at an inclination so its longitudinal axis penetrates the axial gap. The driving shaft of the care head, in turn, is supported in multiple places in the shank.

A turning movement of the driving shaft and the driving pivot results in an oscillatory turning movement of this driving shaft through the engagement of the driving pivot into the axial gap of the rotationally supported driving shaft of the care head. In order to make possible such a movement the length of the axial gap must be greater than the diameter of the circular movement executed by the driving pivot within the axial gap. In order for the care head to function faultlessly, the rotational axes of the driving shaft supported in the shank and the driving shaft of the care head and the longitudinal axis of the driving pivot must virtually intersect in one point. Moreover, the two rotational axes must be disposed at right angles with respect to one another. The slightest deviations from this geometry can lead to an increased wear of the elements involved in the force conversion or to a canting misalignment of the driving pivot in the axial gap. In order to reduce as much as possible the play between the driving element, the bearing of the driving shaft of the care head and of the bearing of the driving shaft in the shank must be manufactured with very high tolerances. The outer bearing site of the driving shaft disposed in the shank must also be in closest possible proximity to the driving pivot. Moreover, dimensional and tolerance accuracy of the housing and bearing parts produced must be high. This is often hard in parts produced in an injection molding process.

The present invention discloses a dental care device without the disadvantages demonstrated regarding prior art devices. The present invention has a force converter which comprises a gymbal supported conversion element in which the driving element which engages the conversion element is fully supported. The rotational axes of the two gymbal bearings of the conversion element are disposed such that they form a right angle and intersect virtually in one point. The conversion element is swivellably supported by a mounting in which the conversion element is centered about one of the two rotational axes of the gymbal bearing; and the mounting is supported turnably about the other rotational axis of the gymbal bearing and carries the care head.

SUMMARY OF THE INVENTION

The primary aspect of the present invention is to provide a dental care device with lower parts tolerances than the prior art.

Other aspects of this invention will appear from the following description and appended claims, reference being made to the accompanying drawings forming a part of this specification wherein like reference characters designate corresponding parts in the several views.

In the present invention the conversion element is mounted in a gymbal bearing assembly such that it is movable about two rotational axes. A component of the gymbal bearing is a mounting in which the conversion element is swivellable about the first rotational axis of the gymbal bearing. The mounting is then supported turnably about the second rotational axis in an encompassing housing, and it carries the care head. The driving element of the driving shaft engages into a recess in the conversion element and is supported therein. With a turning movement of the driving shaft and the driving element the rotational driving movement is resolved into a first oscillatory swivel movement of the conversion element about the first rotational axis, with which the conversion element is supported in the mounting, and into a second oscillatory turning movement of the mounting supported in turn about the second rotational axis of the gymbal bearing.

By developing defined bearing sites for the conversion of the rotational driving movement in the present invention there is no danger of wear or canting. Since the driving element is supported in the conversion element, it is fundamentally not necessary, as is the case within known prior art, to provide bearings disposed in the direct proximity of the care head of the driving shaft disposed in the shank. Rather, it is sufficient and also useful if the driving shaft in the shank is only supported in a position remote from the care head. By having the driving element as a portion of the driving shaft supported in the conversion element, the driving shaft is also supported on this end once the driving element has been brought into engagement position with the conversion element. Since the driving shaft is only properly supported after its engagement in the conversion element, tolerances can readily be accommodated and compensated. Consequently, the tolerances which must be observed in the production of the individual structural parts, in particular of the housing parts, are considerably lower than is the case with the prior art. These lower tolerances reduce the cost of the manufactured item. The bearing of the driving elements in the conversion element also results in wear at this site being virtually eliminated, thus adding to the product life.

The conversion element can be supported by two axle stubs formed such that they are opposing one another diametrically, wherein the axle stubs each engage into a bearing opening of the mounting. The bearing openings can be disposed in two parallel arms of the mounting. When the arms penetrate through the housing of the brush head and are directly joined to a base plate and not connected with one another at the underside, it is useful to provide one or several limitation members. These limitation members are disposed such that pulling the arms of the mounting from the axle stubs engaging the conversion element is prevented. In the event of excessive tension onto the mounting, for example through the attempt of pulling off the care head from the mounting, the arms could otherwise possibly unbend and release the conversion element.

In a preferred embodiment the dental care device is developed as a tooth brush, wherein the care head carries bristle tufts in a plane disposed at right angles to the rotational axis of the mounting. The longitudinal extension of the bristle tufts extends substantially parallel to the rotational axis of the mounting.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE DRAWINGS

Figure 1:
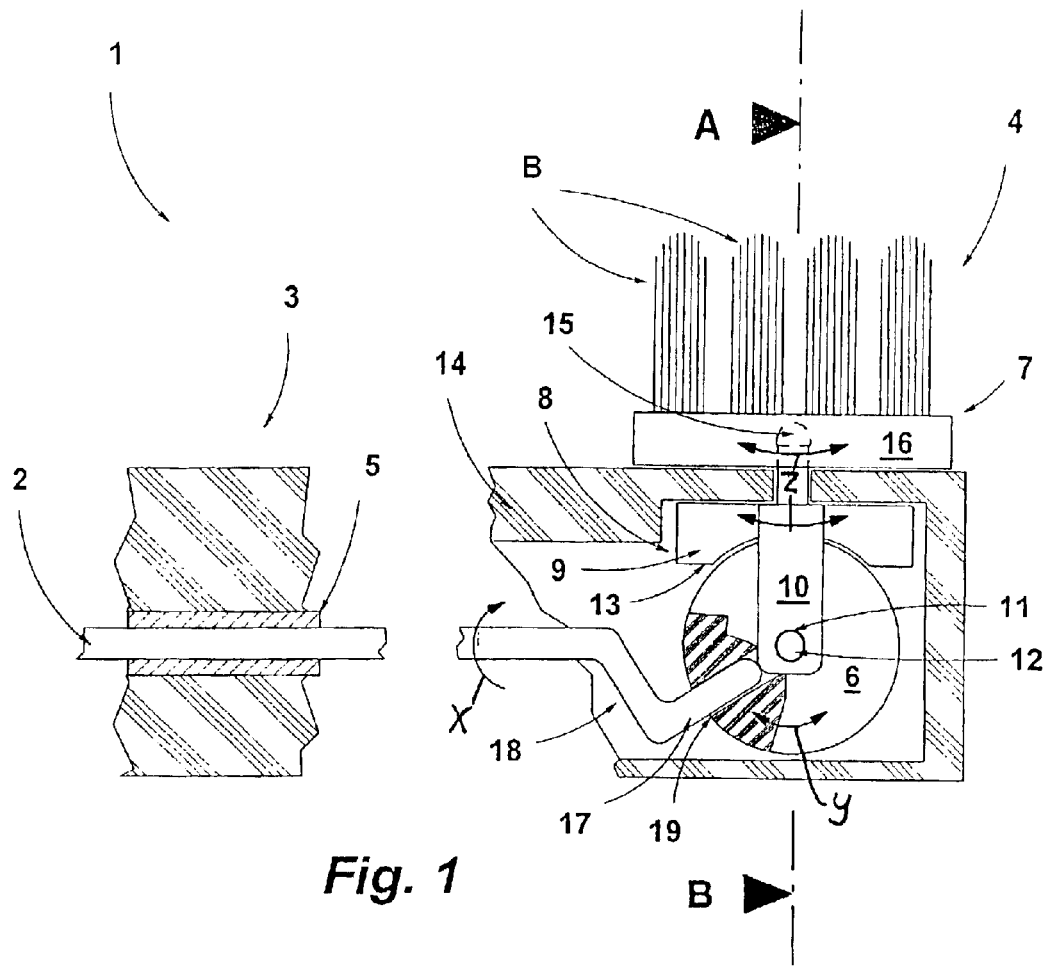
FIG. 1 is a longitudinal section through a schematic of the preferred embodiment.
Figure 2:
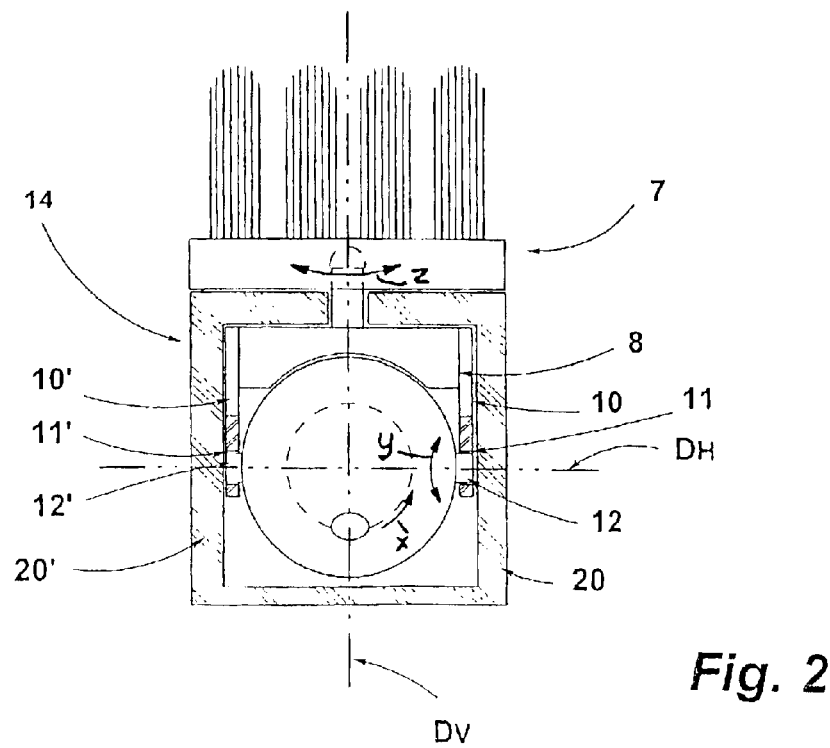
FIG. 2 is a section through the dental care device of FIG. 1 taken along line A-B.

As seen in FIGS. 1 and 2, an electric toothbrush 1 is driven by an electromotor integrated in a handle portion (not shown). The electromotor rotationally drives a driving shaft 2. The driving shaft 2 penetrates through a shank 3, which connects the handle of the toothbrush 1 with a brush head 4. In the shank 3 the driving shaft 2 is supported in its end region next to the handle by a bearing sleeve 5.

The brush head, denoted overall by the reference number 4, represents the front free end of the shank 3. Within the brush head 4 is disposed a conversion element 6 for the conversion of the rotational turning movement of the driving shaft 2 into an oscillatory turning movement of the brush 7 proper. The conversion element 6 is gymballed in the brush head 4 and is carried by a mounting 8. The mounting 8 is formed by an upper plate-like element 9 with downwardly projecting arms 10, 10' in a diametrically opposing configuration, also seen in FIG. 2. Each arm 10, 10' has a bearing opening 11, 11', in which is supported an axle stub 12, 12', formed on the conversion element 6. Through this bearing the conversion element 6 is swivellable about a rotational axis $D_H$ extending horizontally in the Figures. The conversion element 6 is overall developed in the form of a ball and engages with its upper region into the correspondingly shaped underside 13 of the plate-like element 9 of mounting 8.

Figure 3:
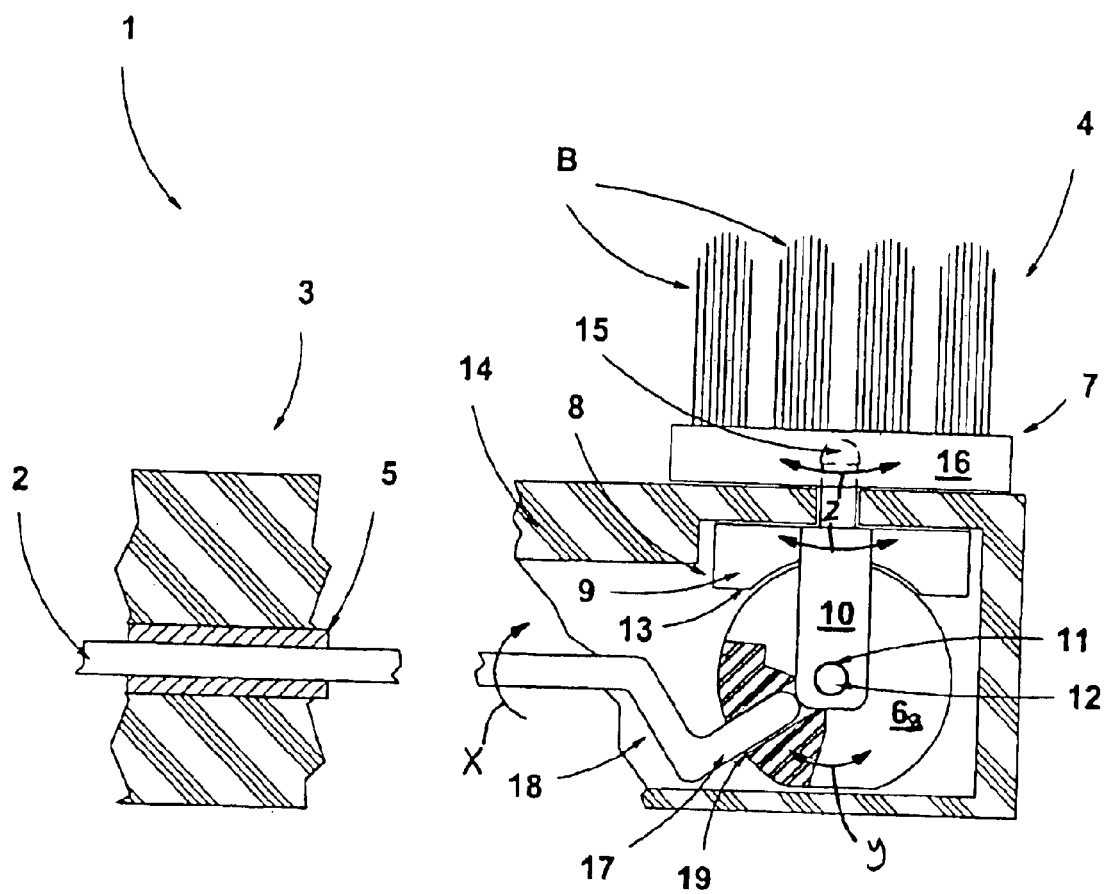
FIG. 3 is a longitudinal section through a schematic of an alternate embodiment.

In one embodiment shown in FIG. 3 the conversion element 6a is a ball having a flattened underside. The ball-form of at least the upper portion of the conversion elements, 6, 6a serves as a staying face, which engages into an arched underside 13 of the mounting to absorb forces acting onto the conversion elements, 6, 6a in this direction. The flattened underside serves to reduce the structural space needed in the final product.

The mounting 8 is supported turnably in the housing 14 of the brush head 4, such that through this bearing forms the second gymbal rotational axis $D_V$ extending vertically in the depicted embodiment example. The two rotational axes $D_H$, $D_V$ are disposed at right angles with respect to one another. Mounting 8 carries an upper extension 15, on which the brush 7 with its base plate 16 is fastened torsion-tight. The base plate 16 carries several bristle tufts B.

On the free end of the driving shaft 2 is disposed as the driving element, a driving pivot 17, whose longitudinal axis extends at an inclination to the rotational axis of the driving shaft 2. The driving pivot 17 is connected to the driving shaft 2 through a crank 18. The driving pivot 17 engages into a bore 19 of the conversion element 6. The driving pivot 17 is supported in the bore 19. The driving element of the driving shaft 17 can also be developed in the manner of a ball head.

During operation the driving shaft 2 rotates as shown by arrow X in FIG. 1. The rotational turning movement of the driving shaft 2 is resolved through the conversion element 6 into two oscillatory turning movements about the two gymbal rotational axes $D_H$ and $D_V$, as shown by arrows Y and Z, respectively. In operation the bore 19 of the conversion element 6 and the driving pivot 17 of driving shaft 2 describe a circular path. This movement is resolved through the gymballing [suspension] of the conversion element 6 into an oscillatory turning movement of the conversion element 6 about the rotational axis $D_H$, arrow Y, as well as into an oscillatory turning movement of mounting 8 about the rotational axis $D_V$, arrows Z, including the conversion element 6 and brush 7 supported by mounting 8.

In the engagement position shown in FIG. 1 between the driving shaft 2 or driving pivot 17 and the conversion element 6, the longitudinal axis of the driving pivot 17 intersects the two rotational axes $D_H$, $D_V$, in its virtual intersection. As shown in FIG. 1, the driving shaft 2 via the driving pivot 17 being set in bore 19 of the conversion element 6 is satisfactorily supported at the side of the brush head 4. A further support of the driving shaft 2 in the region of brush head 4 is thus not necessary. Therefore, the driving shaft 2 of the toothbrush 1 is only supported at a single site, as described above, in the shank 3. If the driving shaft is supported in the handle of the toothbrush, a further bearing within the shank fundamentally also does not need to be provided.

The housing 14 of brush head 4 is developed such that it is relatively narrow in the region of the two arms 10, 10', in order prevent the pulling-off of the arms 10, 10' from the axle stubs 12, 12'. Such an implementation is suitable in particular when the arms of the mounting are guided through the housing of the brush head and are directly connected with the base plate of the brush. In this case the side walls 20, 20' of housing 14 represent the limitation members for arms 10, 10' of mounting 8. The side walls 20, 20' are drafted such that these have a constant distance to the outer sides of the arms 10, 10' over the entire swivel amplitude of arms 10, 10' about the rotational axis $D_V$. Instead of a development of the side walls 20, 20' as limitation members, in the housing 14 a corresponding open ring can also be disposed as the limitation member.

Although the present invention has been described with reference to preferred embodiments, numerous modifications and variations can be made and still the result will come within the scope of the invention. No limitation with respect to the specific embodiments disclosed herein is intended or should be inferred.

| List of Reference Symbols | |
| --- | --- |
| 1 | Toothbrush |
| 2 | Driving shaft |
| 3 | Shank |
| 4 | Brush head |
| 5 | Bearing sleeve |
| 6 | Conversion element |
| 7 | Brush |
| 8 | Mounting |
| 9 | Plate-like element |
| 10, 10' | Arm |
| 11, 11' | Bearing opening |
| 12, 12' | Axle stub |
| 13 | Underside |
| 14 | Housing |
| 15 | Extension |
| 16 | Base plate |
| 17 | Driving pivot |
| 18 | Crank |
| 19 | Bore |
| 20, 20' | Side wall |
| B | Bristle tuft |
| $D_H$ | Rotational axis [horizontal] |
| $D_V$ | Rotational axis [vertical |

I claim:

1. An electric dental care device with a care head oscillatingly driven about a rotational axis, the electric dental care device comprising:

a rotationally driven driving shaft with a driven end, said driven end having a driving element disposed eccentrically with respect to a rotational axis of the driving shaft;

a force converter having a gymbal support, said support comprising two gymbal bearings creating a first and second rotational axis each disposed such that the axes form a right angle to each other and intersect virtually in one point;

the first gymbal bearing comprising:

a mounting attached to the care head and rotatably supported about the second rotational axis;

a conversion element rotatably supported by the second gymbal bearing in the mounting about the first axis and having a recess shaped to receive the driving element;

the driving element engaged into the recess of the conversion element and supported thereby, thereby converting a rotational driving force of the driven driving shaft into an oscillatory turning movement of the care head.

2. The dental care device of claim 1, wherein the conversion element is developed in the form of a ball with a flattened underside facing away from the care head.

3. The dental care device of claim 1, wherein the side facing the care head of the conversion element engages into an arched underside of the mounting.

4. The dental care device as claimed in claim 1, 2 or 3, wherein the second gymbal bearing further comprises formed-on axle stubs on the conversion element diametrically opposing one another, which engage into correspondingly shaped bearing openings on the mounting.

5. The dental care device as claimed in claim 4, wherein the bearing openings of the mounting are disposed in arms and wherein one or several limiting members are provided to prevent the pulling-off of the arms from the axle stubs of the conversion element.

6. The dental care device as claimed in claim 4, wherein the mounting in a housing of the dental care device and the driving shaft in a shank associated with the dental care device is supported on only one site markedly spaced apart from the care head.

7. The dental care device as claimed in claim 4, wherein the driving element is a driving pivot whose longitudinal axis is inclined relative to the rotational axis of the driving shaft and which is connected via a crank with the driving shaft, and that the driving pivot engages into the recess the conversion element.

8. The dental care device as claimed in claim 7, wherein the longitudinal axis of the driving pivot intersects the virtual intersection of the two rotational axes of the force converter.

9. The dental care device as claimed in claim 4, wherein the care head further comprises bristle tufts in a plane disposed at right angles to the first rotational axis of the force converter and which extend substantially parallel to the second rotational axis the force converter.

* * * * *